United States Patent [19]

O'Lenick, Jr.

[11] Patent Number: 5,756,785
[45] Date of Patent: May 26, 1998

[54] GUERBET BETAINES

[75] Inventor: Anthony J. O'Lenick, Jr., Lilburn, Ga.

[73] Assignee: Lambent Technologies, Inc., Norcross, Ga.

[21] Appl. No.: 822,624

[22] Filed: Mar. 21, 1997

[51] Int. Cl.$^6$ .................................................. C07C 233/00
[52] U.S. Cl. ............................... 554/52; 584/35; 584/58
[58] Field of Search .................... 584/35, 52, 58

[56] References Cited

U.S. PATENT DOCUMENTS 4,490,355  12/1984  Desai .
5,488,121  1/1996  O'Lenick, Jr. .

OTHER PUBLICATIONS

Morrison & Boyd, Organic Chemistry, 4th ed., p. 828, 1983.

*Primary Examiner*—Gary Geist
*Assistant Examiner*—Deborah D. Carr

[57] ABSTRACT

The present invention deals with the composition of matter and the utilization of certain novel guerbet based betaine compounds. These materials are useful in personal care applications.

11 Claims, No Drawings

GUERBET BETAINES

BACKGROUND OF THE INVENTION

1. Field of the Invention

The present invention deals with novel, surfactants, specifically betaines, based upon highly branched guerbet acids.

2. Description of the Art Practices

Guerbet alcohols have been known for many years. Over the years there have been a number of derivatives patented. These materials can be oxidized into acids, which are raw materials for the preparation of the specific complex esters of the present invention. They possess the critical regiospecific guerbet linkage which when placed into amidoamine compounds and betaines derived therefrom result in unexpected improvements in both liquidity oxidative stability.

U.S. Pat. No. 5,488,121 to O'Lenick, incorporated herein by reference, discloses di-guerbet esters based upon the reaction product of both a guerbet acid and a guerbet alcohol. The guerbet acids of that invention are raw materials used in the preparation of the compounds of the present invention.

U.S. Pat. No. 4,490,355 to Desai, describes a mixture of a cocamidopropyl betaine and oleamidopropyl betaine. This blend was made to improve thickening in cosmetic products. The improved viscosity is attained by the incorporation of the oleyl species (C18 unsaturated). This art shows that viscosity building is a long felt need in the market. The oleyl type of unsaturation found in this approach causes the rancidity problem discussed in the present invention.

1. Field of the Invention

The present invention deals with novel amphoteric surfactants based upon a highly branched guerbet acid. The introduction of the guerbet branch into the betaines of the present invention results in improved viscosity building in personal care formulations as well as improved odor stability in the formulation and improved liquidity of the aqueous betaine per se.

2. Description of the Art Practices

Betaines are known in the art. Variation of carbon chain lengths in amido betaines has direct effect upon the surfactant properties of the betaine. While amido betaines based upon short chain fatty acids can be made, they do not produce foam, nor have conditioning effects on hair. The use of fatty acids having more that 12 carbon atoms to make betaines result in betaines which provide better aqueous foam, but little or no conditioning and a limited ability to build viscosity when formulated together with anionic surfactants. Anionic systems are very commonly used in shampoos, body washes, hand detergents and other personal care products. Consumer perception and acceptance of these personal care products is in part based upon the feel on the skin and the thickness of the resulting formulation. Betaines like cocamidopropyl betaine can be used with some success in formulations based upon alpha olefin sulfonate. They simple do not build sufficient viscosity. The selection of a oleyl amido betaine gives some improved viscosity, but the compound undergoes a process of oxidative instability referred to as rancidity, producing low molecular weight aldehydes with mal odor. The availability of a liquid, oxidatively stable betaine that can be used in personal care systems has been elusive prior to the compounds of the present invention.

The recent availability of guerbet acids and their reaction to make betaines results in the preparation liquid stable betaines, having outstanding emulsifying properties and are very acceptable for use in personal care applications.

None of the prior betaines possess the critical guerbet moiety. Molecules of the current invention have the guerbet group in the betaine.

THE INVENTION

This invention relates to the use of a guerbet acid to make an guerbet alkyl amidopropyl dialkyl betaine, which has unique, unexpected properties in personal care applications. Specifically, the betaines of the present invention provide a smooth feel on the skin, outstanding viscosity in anionic systems, and are surprisingly oxidatively stable in aqueous personal care formulations.

Another aspect of the present invention is the guerbet amidopropyl dialkyl amine intermediate useful as an intermediate in the preparation of the betaine of the present invention and other surfactant derivatives.

The compounds of the current invention are betaines derived from guerbet acid and conform to the following structure;

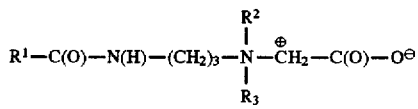

wherein:

$R^1$ is

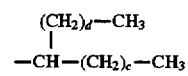

c and d are independently integers ranging from 3 to 17; $R^2$ and $R^3$ are methyl or ethyl.

The betaine is prepared in a two step reaction. The first step is the preparation of a guerbet amidoamine conforming to the following structure:

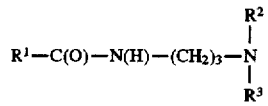

wherein:

$R^1$ is

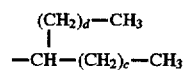

c and d are independently integers ranging from 3 to 17. The reaction is as follows:

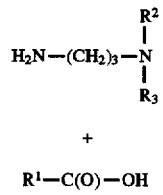

-continued

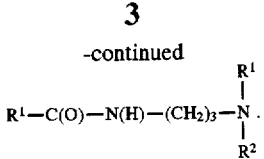

As previously stated another novel aspect of the present invention is the amidoamine intermediate conforming to the following structure:

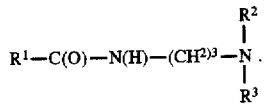

wherein:
$R^1$ is

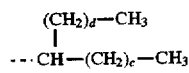

c and d are independently integers ranging from 3 to 17.

In the second reaction the amidoamine, prepared in the first reaction, is reacted in aqueous solution with of sodium chloroacetate as follows:

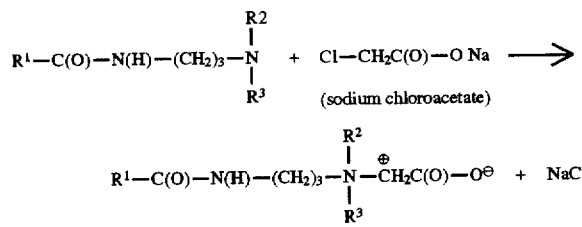

The concentration of the betaine in water is generally between 20 and 50% with 35% being preferred. Glycols, lower alcohols and other polar solvents may also be added, if desired.

EXAMPLES

Raw Materials

Guerbet Acids

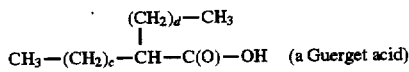

Vista Chemical practices the oxidation of guerbet alcohols commercially. The values of c and d were actually determined by analysis and are not dependant upon trade name for meaning.

| Example | Commercial Name | c | d |
|---------|-----------------|----|----|
| 1 | Isocarb 10 | 3 | 3 |
| 2 | Isocarb 12 | 4 | 4 |
| 3 | Isocarb 14 | 5 | 5 |
| 4 | Isocarb 16 | 6 | 6 |
| 5 | Isocarb 18 | 7 | 7 |
| 6 | Isocarb 20 | 8 | 8 |
| 7 | Isocarb 32 | 14 | 14 |
| 8 | Isocarb 40 | 17 | 17 |

Isocarb is a trademark of Vista.

Aminopropyl Amine

The compounds conform to the following structure:

Example 9 Dimethyl aminopropyl amine

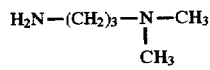

Example 10 Diethyl aminopropyl amine

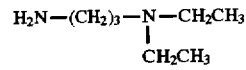

General Procedure

To the specified number of grams the specified dialkyl aminopropyl amine (Examples 9 and 10) is added the specified number of grams of the specified guerbet acid (examples 1–9) under agitation. The temperature of the mass is raised to 180°–200° C. and water is stripped off as formed. This temperature is held for between 1 and 12 hours. The acid value and the primary amine value drops to vanishingly small levels and the tertiary amine level approaches theoretical.

The products are clear liquids and are liquid to extraordinary temperatures.

| | Guerbet Acid | | Aminopropyl Amine | |
|---------|---------|-------|---------|-------|
| Example | Example | Grams | Example | Grams |
| 11 | 1 | 171.0 | 9 | 122.0 |
| 12 | 2 | 199.0 | 9 | 122.0 |
| 13 | 3 | 227.0 | 9 | 122.0 |
| 14 | 4 | 255.0 | 9 | 122.0 |
| 15 | 5 | 283.0 | 9 | 122.0 |
| 16 | 6 | 311.0 | 9 | 122.0 |
| 17 | 7 | 479.0 | 9 | 122.0 |
| 18 | 8 | 592.0 | 9 | 122.0 |
| 19 | 1 | 171.0 | 10 | 150.0 |
| 20 | 2 | 199.0 | 10 | 150.0 |
| 21 | 3 | 227.0 | 10 | 150.0 |
| 22 | 4 | 255.0 | 10 | 150.0 |
| 23 | 5 | 283.0 | 10 | 150.0 |
| 24 | 6 | 311.0 | 10 | 150.0 |
| 25 | 7 | 479.0 | 10 | 150.0 |
| 26 | 8 | 592.0 | 10 | 150.0 |

The compounds are the intermediate conforming to the following structure:

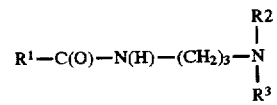

Betaine Synthesis

To the specified number of grams of sodium chloroacetate is added to the specified amount of water. The solution is heated to 80° C. and the amidoamine (examples 11–26) is added under agitation. The pH is kept between 8–9 by adding NaOH as required. The reaction progress is monitored by the inorganic chloride level, which within 3–4 hours reaches theoretical.

Example 27

To the 137.0 grams of sodium chloroacetate is added 1,000 grams of water. The solution is heated to 80° C. and 438.0 293.0 grams of amidoamine (example 27) is added under agitation. The pH is kept between 8–9 by adding NaOH as required. The reaction progress is monitored by the inorganic chloride level, which within 3-4 hours reaches theoretical.

Examples 28-42

Example 27 is repeated, only this time the specified amount and type of amido amine is substituted for the amido amine of example 27.

|         | Amidoamine |       |
|---------|------------|-------|
| Example | Example    | Grams |
| 28      | 12         | 321.0 |
| 29      | 13         | 349.0 |
| 30      | 14         | 377.0 |
| 31      | 15         | 405.0 |
| 32      | 16         | 433.0 |
| 33      | 17         | 601.0 |
| 34      | 18         | 714.0 |
| 35      | 19         | 320.0 |
| 36      | 20         | 351.0 |
| 37      | 21         | 399.0 |
| 38      | 22         | 407.0 |
| 39      | 23         | 435.0 |
| 40      | 24         | 470.0 |
| 41      | 25         | 631.0 |
| 42      | 26         | 743.0 |

The products produced using the examples 27-42 are clear yellow viscous liquids. The products have outstanding oxidative stability and provide outstanding viscosity when formulated in alpha olefin sulfonate containing systems.

I claim:

1. A guerbet betaine which conforms to the following structure:

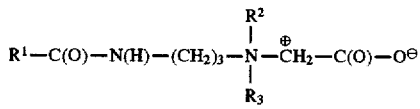

wherein:

$R^1$ is

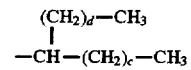

c and d are independently integers ranging from 3 to 17.
$R^2$ and $R^3$ are methyl or ethyl.

2. A guerbet betaine of claim 1 wherein $R^2$ is methyl.
3. A guerbet betaine of claim 1 wherein $R^2$ is ethyl.
4. A guerbet betaine of claim 1 wherein c is 3 and d is 3.
5. A guerbet betaine of claim 1 wherein c is 4 and d is 4.
6. A guerbet betaine of claim 1 wherein c is 5 and d is 5.
7. A guerbet betaine of claim 1 wherein c is 6 and d is 6.
8. A guerbet betaine of claim 1 wherein c is 7 and d is 7.
9. A guerbet betaine of claim 1 wherein c is 8 and d is 8.
10. A guerbet betaine of claim 1 wherein c is 14 and d is 14.
11. A guerbet betaine of claim 1 wherein c is 17 and d is 17.

* * * * *